United States Patent [19]

Freeman

[11] Patent Number: 4,816,023

[45] Date of Patent: Mar. 28, 1989

[54] OSTOMY COUPLING HAVING INTEGRAL O-RING COUPLING

[75] Inventor: Frank M. Freeman, Lawrenceville, N.J.

[73] Assignee: E. R. Squibb & Sons, Inc., Princeton, N.J.

[21] Appl. No.: 121,387

[22] Filed: Nov. 16, 1987

[51] Int. Cl.⁴ .............................................. A61F 5/44
[52] U.S. Cl. .................................................... 604/339
[58] Field of Search ................................ 604/332–345, 604/277; 285/921, 383; 220/378

[56] References Cited

U.S. PATENT DOCUMENTS

| | | | |
|---|---|---|---|
| 4,460,363 | 7/1984 | Steer et al. | 604/339 |
| 4,518,389 | 5/1985 | Steer et al. | 604/339 |
| 4,559,048 | 12/1985 | Steer | 604/338 |
| 4,592,750 | 6/1986 | Kay | 604/277 |

Primary Examiner—C. Fred Rosenbaum
Assistant Examiner—J. L. Kruter
Attorney, Agent, or Firm—Lawrence S. Levinson; Robert E. Lee, Jr.

[57] ABSTRACT

The present invention is an improved coupling for as ostomy bag system. In the improved coupling, an integral O-ring is included to improve the retention of the coupling as well as its seal by extending through the annular ring.

4 Claims, 6 Drawing Sheets

OSTOMY COUPLING HAVING INTEGRAL O-RING COUPLING

BACKGROUND OF THE INVENTION

The present invention relates to a coupling device. In particular, the invention relates to a two-piece, O-ring coupling design which can be used to seal an ostomy pouch to a body side flange.

Ostomy couplings are used to connect body side flanges, which are typically adhesively attached to the body of a wearer, to matching couplings which are typically attached to disposable bags.

It is quite important that the seal between the body side member and the bag side member be secure, and to the extent possible, be free of leakage of gases or fluids.

SUMMARY OF THE INVENTION

The present invention is an ostomy coupling comprised of a bag side flange and a body side flange. The body side flange includes an annular ring having a central aperture designed to surround a stoma and including a relatively wide flange to which an adhesive material for attachment to the body of the wearer. The body side flange includes an integral O-ring made of a resilient material. The bag side flange includes an annular ring adapted to lock onto the body side flange in a manner which compresses the O-ring to provide a resilient seal.

DETAILED DESCRIPTION OF THE PREFERRED EMBODIMENT

Figure 1:
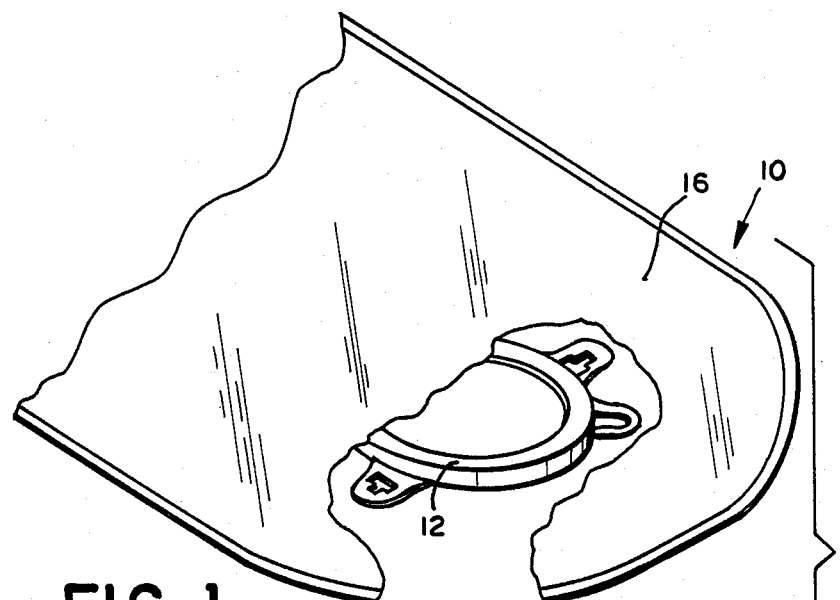
FIG. 1 is a perspective view illustrating the body side flange and bag side flange of a first embodiment of the present invention.
Figure 2:
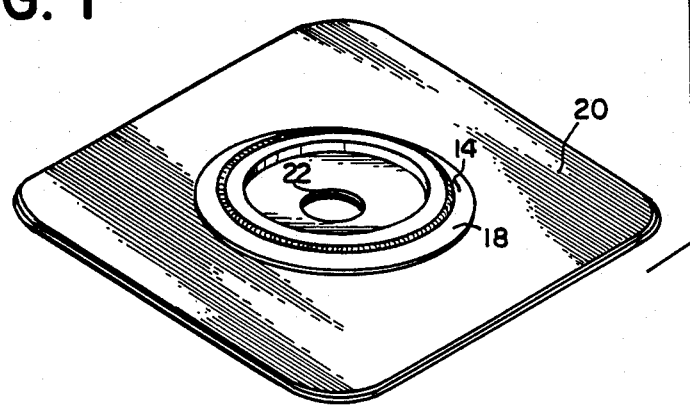
FIG. 2 is a side cross-sectional view of the body side flange and bag side flange shown in FIG. 1.
Figure 2:
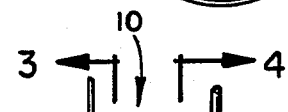
Figure 2:
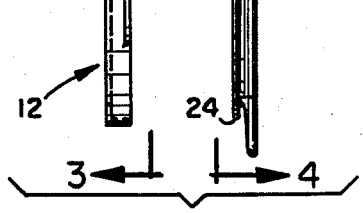
Figure 3:
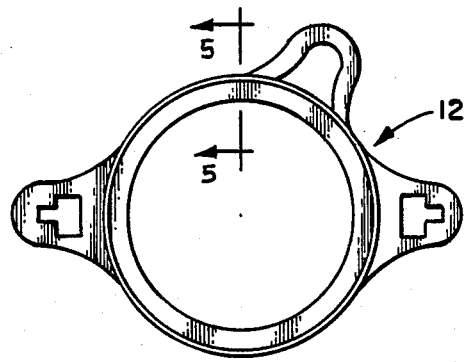
FIG. 3 is a bottom view of the bag side flange of the embodiment shown in FIG. 1 taken along the lines 3—3 of FIG. 2.
Figure 4:
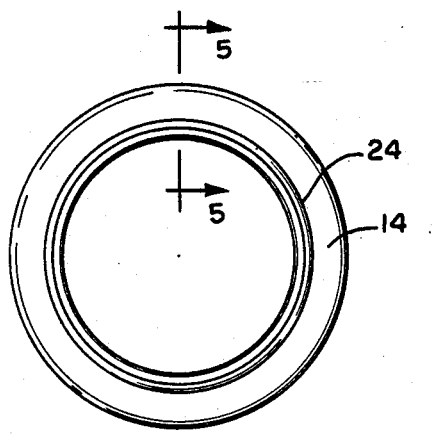
FIG. 4 is a top view of the body side flange of FIG. 1 taken along the lines 4—4 of FIG. 2.

Referring to FIGS. 1-5, the first embodiment of an ostomy coupling 10 made in accordance with the present invention, is shown. The ostomy coupling 10 is comprised of a bag side member 12 and a body side member 14. As is standard in the art, the bag side member 12 is attached to an ostomy bag 16, and the body side member 14 includes a flange 18 which is used to attach the body side member 14 to a pad of adhesive 20 for use in attaching the body side member 14 to the body of a wearer (not shown). The body side member 14 includes an opening 22 which overlies a similar opening which is formed in the adhesive pad 20. These openings 22 are placed over the stomal opening of the wearer.

Figure 5:
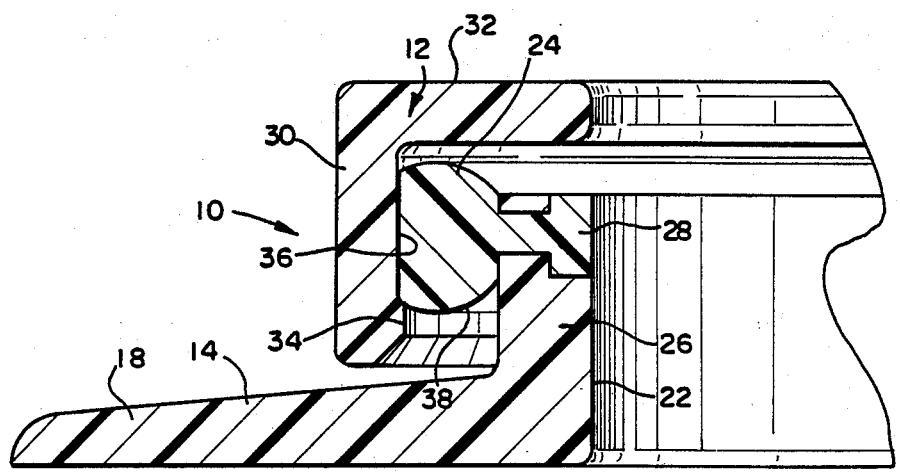
FIG. 5 is a cross-sectional view showing the assembled bag side flange and body side flange of FIG. 1.
Figure 6:
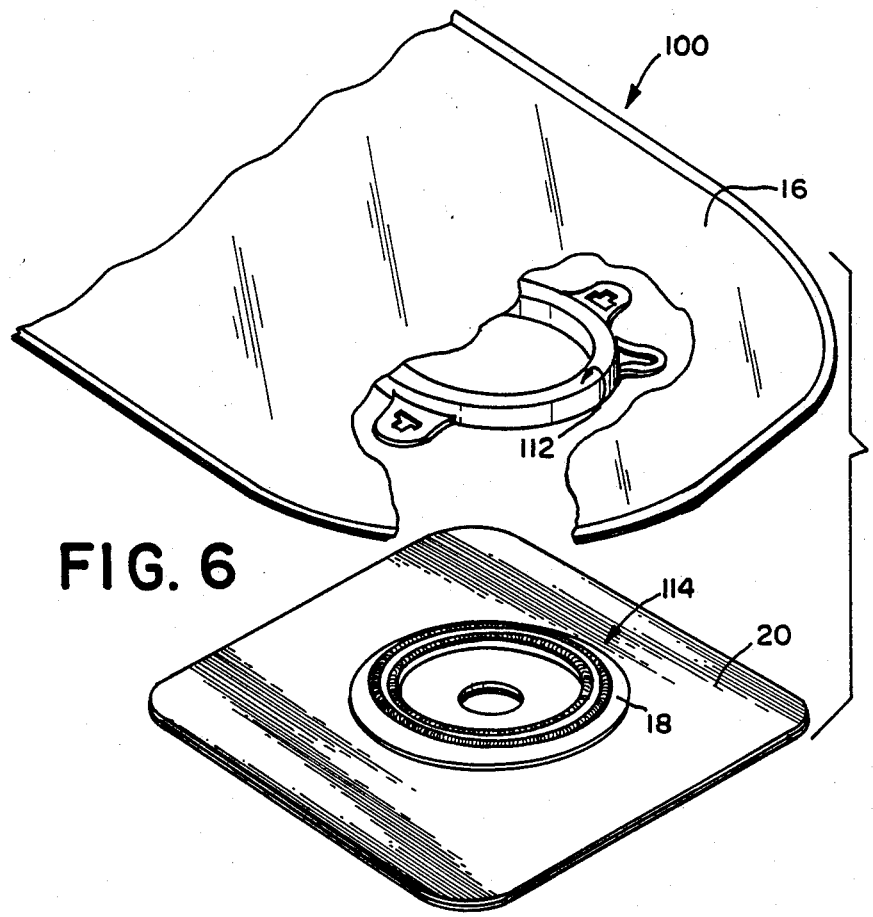
FIG. 6 is a perspective view illustrating the body side flange and bag side flange of a second embodiment of the present invention.
Figure 7:
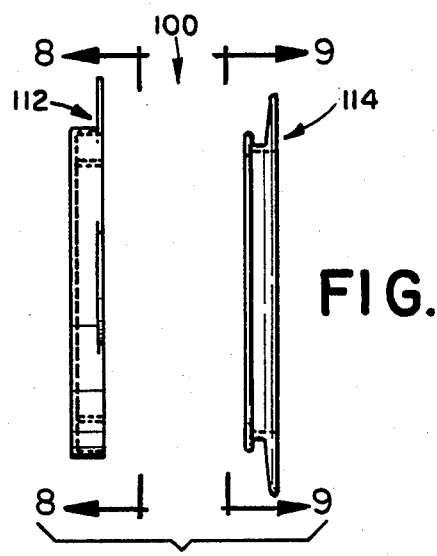
FIG. 7 is a side cross-sectional view of the body side flange and bag side flange shown in FIG. 6.
Figure 8:
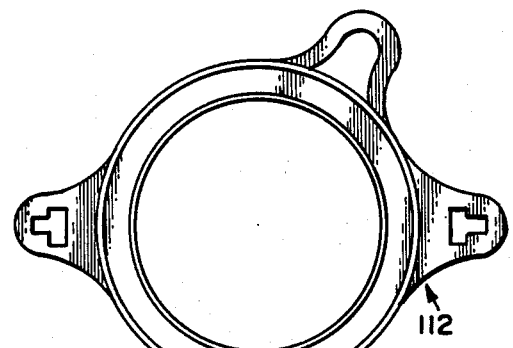
FIG. 8 is a bottom view of the bag side flange of the embodiment shown in FIG. 6 taken along the lines 5—5 of FIG. 7.
Figure 9:
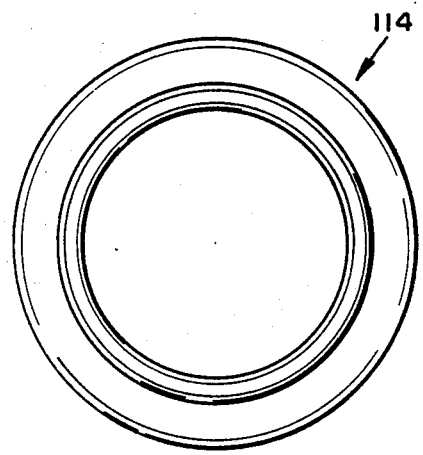
FIG. 9 is a top view of the body side flange of FIG. 6 taken along the lines 6—6 of FIG. 7.
Figure 10:
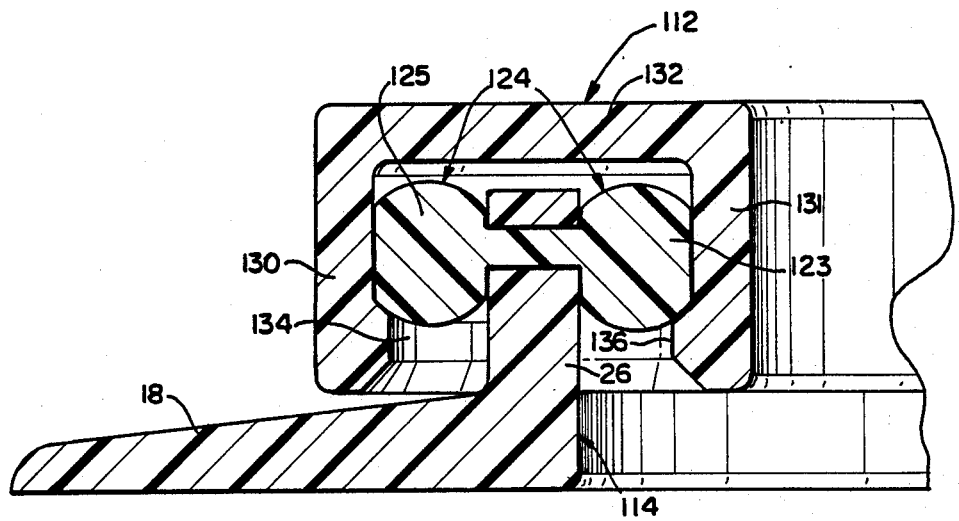
FIG. 10 is a cross-sectional view showing the assembled bag side flange and body side flange of FIG. 6.
Figure 11:
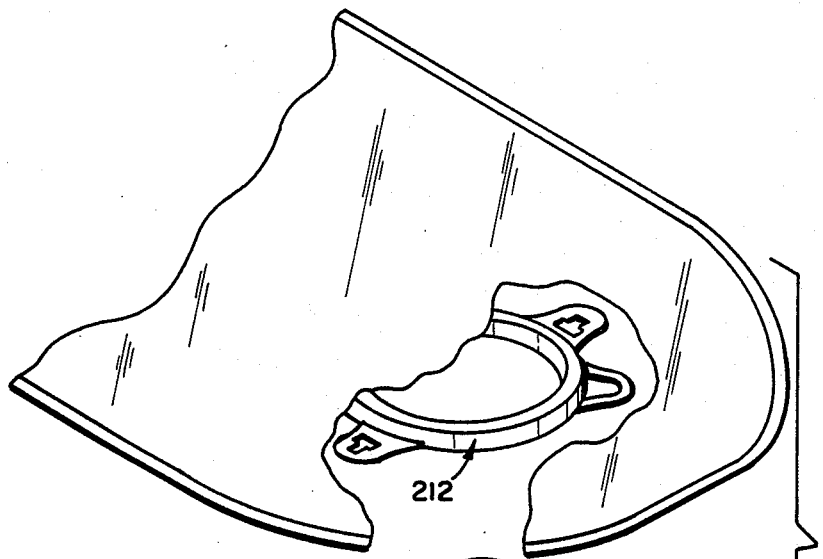
FIG. 11 is a perspective view illustrating the body side flange and bag side flange of a third embodiment of the present invention.
Figure 12:
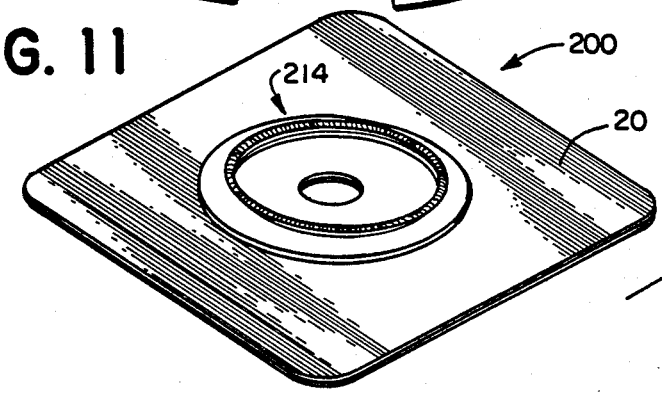
FIG. 12 is a side cross-sectional view of the body side flange and bag side flange shown in FIG. 11.
Figure 12:
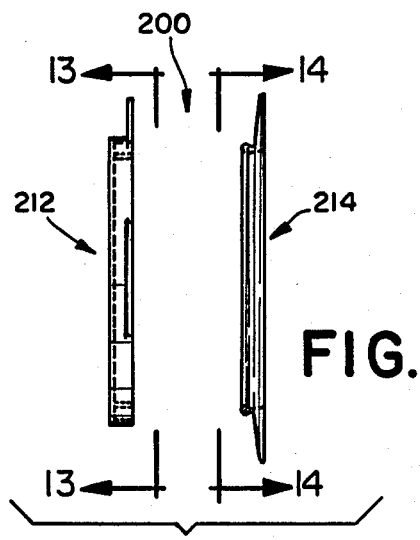
Figure 13:
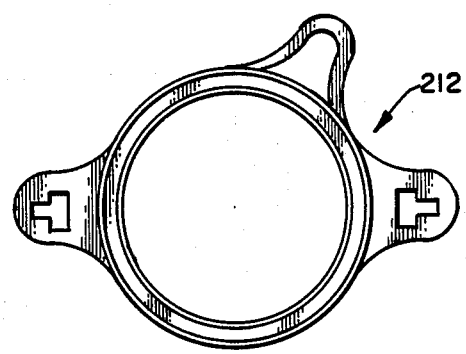
FIG. 13 is a bottom view of the bag side flange of the embodiment shown in FIG. 11 taken along the lines 7—7 of FIG. 12.
Figure 14:
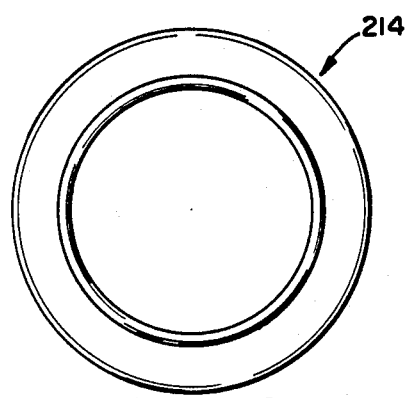
FIG. 14 is a top view of the body side flange of FIG. 11 taken along the lines 8—8 of FIG. 12.
Figure 15:
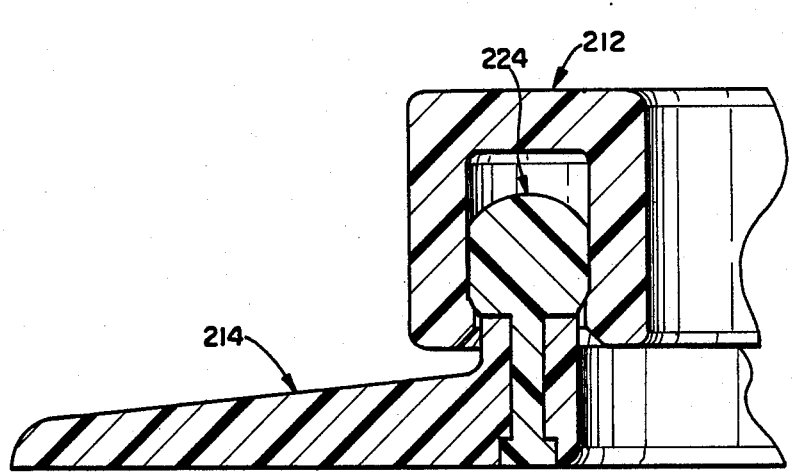
FIG. 15 is a cross-sectional view showing the assembled bag side flange and body side flange of FIG. 11.

As will be shown, the present invention is unique in that it contemplates the use of an seal which includes an O-ring 24 which is made to be an integral part of the coupling 10. Referring particularly to FIG. 5, the body side member 14 further comprises an interior cylindrical wall 26 which is made to be an integral part of the body side member 14 and which surrounds the stomal opening 22. The integral O-ring 24 surrounds the wall 26 and is coupled thereto by a series of T-shaped (cross-section) attachment means 28 which extend through the wall 26 and securely fasten the O-ring 24 thereto. These attachment means 28 are formed as part of the O-ring 24, and the bag side flange 12 is molded with the O-ring 24 inserted into the mold, thereby assuring the integrity of the completed bag side member 12 and O-ring 24 combination. The O-ring coupling design of the present invention is used to create a removable liquid tight seal between the two members 12 and 14. In use, the O-ring 24 is contacted by a cylindrical leg 30 which extends downward from a bag attachment flange 32 on the bag side member 12. This type of coupling provides a very reliable, easy to couple seal. Integral molding of the O-ring 24 into the body side member 14 assures complete security of the O-ring 24.

With particular reference to FIG. 5, the bag side flange 12 includes a shoulder 34 which is on the inner surface of the cylindrical leg 30. The shoulder 34 cooperates with the O-ring 24 when the flanges 12, 14 are pressed together. As the O-ring 24 passes the shoulder 34 a "snap" will be heard and felt indicating that a sealing engagement has been accomplished. The inner surface 36 of the wall 30 and the outer surface 38 of the wall 26 have less space between them than the diameter of the O-ring 24. Accordingly, when the flanges 12, 14 are "snapped" together, a liquid tight seal is formed.

Referring generally now to FIGS. 6-10, a second embodiment of an ostomy coupling 100 in accordance with the present invention is shown, the ostomy coupling 100 is comprised of a bag side member 112 and a body side member 114. The bag side member 112 is connected to a ostomy bag 16, and the body side member 114 includes a flange 18 which is used to attach the body side member 114 to an adhesive pad 120, as in the first embodiment. With reference to FIGS. 7-10, it is clear that the second embodiment is quite similar to the first embodiment of the invention except that the second embodiment uses a dual O-ring 124 including both an inner portion 133 and an outer portion 125 which are inside and outside respectively, the cylindrical wall 26 which is attached to the flange 18.

The bag side member 112 includes both an outer cylindrical leg 130 and an inner cylindrical leg 131, which together with the bag attachment flange 132 form a substantially U-shaped channel which fits over the dual O-ring 124 such that when the bag side member 112 is applied over the dual O-ring 124, the raised annular sections 134, 136 snap over the outer and inner portions 125, 123 of the dual O-ring 124. As will be recognized by one of ordinary skill in the art, the difference in manufacturing the body side member 114 with respect to the body side member 114 of the first embodiment merely involves placing the dual O-ring 124 into the mold prior to forming the flange 18 in wall 26 structure.

Referring now to FIGS. 11–15, yet another embodiment of the present invention 200 is shown. In the embodiment 200, the bag side member 212 is virtually identical to the bag side member 112 of the second embodiment, except that the U-shaped channel is substantially narrower because only a single vertically oriented O-ring 224 is used. The bag side member 214 differs from the body side members of the embodiments 10–100 in that the attachment means extends vertically through the wall 226 rather than horizontally as in the other embodiments 10–100.

We claim:

1. An improved coupling for an ostomy bag of the type comprised of a bag side flange and a body side flange, the improvement comprising:
   (a) the body side flange including a relatively wide flange having an adhesive material for attachment to the body of the wearer and including an annular ring having a central aperture designed to surround a stoma and extending from said flange and the body side flange including an integral O-ring made of a resilient material which encircles the annular ring and is coupled thereto by a series of attachments formed as part of the O-ring and extending through said annular ring; and
   (b) the bag side flange including an annular ring to lock onto the body side flange in a manner which compresses the O-ring to provide a resilient seal.

2. The coupling of claim 1 wherein said bag side annular ring includes a shoulder protruding toward said stoma opening and cooperates with the O-ring to couple said flanges together.

3. An improved coupling for an ostomy bag of the type comprised of a bag side flange and a body side flange, the improvement comprising:
   (a) the body side flange including a relatively wide flange which carries adhesive material for attachment to the body of the wearer, an annular ring having a central aperture designed to surround a stoma and extending from said flange and a dual O-ring including an outer portion which encircles said ring and an inner portion on the inside of said ring, said inside and outside O-ring portions coupled together through said ring; and
   (b) the bag side flange including inner and outer spaced apart annular rings adapted to lock onto the body side flange in a manner which compresses both portions of said O-ring to provide a resilient seal.

4. The coupling of claim 3 wherein said inner and outer annular rings each include shoulders which cooperate with the O-ring portions to couple said flanges together.

* * * * *